US012383756B2

(12) United States Patent
Yang et al.

(10) Patent No.: US 12,383,756 B2
(45) Date of Patent: Aug. 12, 2025

(54) MEDICAL SYSTEMS, DEVICES, AND RELATED METHODS

(71) Applicant: Boston Scientific Scimed, Inc., Maple Grove, MN (US)

(72) Inventors: Jiandong Yang, Pleasanton, CA (US); Venkata Vegesna, Saratoga, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 18/404,545

(22) Filed: Jan. 4, 2024

(65) Prior Publication Data

US 2024/0198125 A1 Jun. 20, 2024

Related U.S. Application Data

(63) Continuation of application No. 16/870,124, filed on May 8, 2020, now abandoned.
(60) Provisional application No. 62/846,195, filed on May 10, 2019.

(51) Int. Cl.
*A61N 5/00* (2006.01)
*A61N 5/06* (2006.01)
*A61N 5/067* (2006.01)

(52) U.S. Cl.
CPC .... *A61N 5/0613* (2013.01); *A61N 2005/0626* (2013.01); *A61N 2005/063* (2013.01); *A61N 5/067* (2021.08)

(58) Field of Classification Search
None
See application file for complete search history.

(56) References Cited

U.S. PATENT DOCUMENTS

| 2004/0114879 | A1* | 6/2004 | Hiereth | A61B 90/98 |
| | | | | 385/88 |
| 2006/0012914 | A1 | 1/2006 | Todd et al. | |
| 2006/0129140 | A1* | 6/2006 | Todd | A61B 90/98 |
| | | | | 606/1 |
| 2010/0138684 | A1 | 6/2010 | Kim et al. | |
| 2013/0041357 | A1 | 2/2013 | Neuberger | |
| 2016/0346058 | A1 | 12/2016 | Bacher et al. | |

(Continued)

FOREIGN PATENT DOCUMENTS

| EP | 3412239 A1 | 12/2018 |
| WO | 2016075613 A1 | 5/2016 |

*Primary Examiner* — Sana Sahand
(74) *Attorney, Agent, or Firm* — Seager, Tufte & Wickhem, LLP (57) ABSTRACT

According to one aspect, a method of controlling a laser delivery control console is disclosed. The method may include receiving at the control console electronically stored information from a radio frequency identification tag associated with a medical device. The method may also include converting, using at least one processor of the control console, the electronically stored information to a plurality of operating parameter threshold values. The plurality of threshold values may include maximum frequency values and maximum energy values for laser energy supplied by the laser delivery control console to the medical device. The method may further include preventing, in response to a command to adjust the energy or frequency of laser energy applied to the medical device, the delivery of laser energy with a frequency or energy value that exceeds one or more of the threshold values.

20 Claims, 6 Drawing Sheets

(56) References Cited

U.S. PATENT DOCUMENTS

| | | |
|---|---|---|
| 2017/0354464 A1* | 12/2017 | Waisman .............. A61B 17/22 |
| 2018/0014872 A1 | 1/2018 | Dickerson |
| 2018/0042676 A1 | 2/2018 | Neuberger et al. |
| 2019/0247680 A1 | 8/2019 | Mayer et al. |

* cited by examiner

MEDICAL SYSTEMS, DEVICES, AND RELATED METHODS

CROSS-REFERENCE TO RELATED APPLICATIONS

This application is a continuation of U.S. Non-Provisional application Ser. No. 16/870,124, filed May 8, 2020, which claims the benefit of priority from U.S. Provisional Application No. 62/846,195, filed on May 10, 2019, which is incorporated by reference herein in its entirety.

TECHNICAL FIELD

Various aspects of the present disclosure relate generally to systems, devices, and methods useful in medical procedures. More specifically, the present disclosure relates to systems, devices, and methods for adjusting and storing operating parameters of medical devices, among other aspects.

BACKGROUND

Laser energy is used in a wide variety of medical procedures, including urology, neurology, otorhinolaryngology, ophthalmology, gastroenterology, cardiology, and gynecology. Various procedures, and even different portions of the same procedure, often require different levels and intensities of laser energy, which are delivered to cauterize, ablate, break-up, or otherwise treat tissue or other material in a patient. Generally, a user may control and/or modify the settings for the laser energy output of a laser energy source by inputting or adjusting the settings of a control module through buttons, dials, or a touch screen. A laser energy source may be operatively coupled to the control module and may comprise laser energy sources which operate at different wavelengths, infrared or visible energy sources, a Holmium laser source, Carbon Dioxide laser source, Neodymium laser source, or other type of laser energy source. Depending on the user's desired energy and frequency levels of the laser energy source, the user may select one or more accessories with operating parameters that allow the user to transmit the desired level and intensity of laser energy through the accessory. Accessories used to transmit laser energy, such as laser fibers, have different operating parameters in which the accessory may function without being damaged by the laser energy. Typically, a database on the control module may store operating parameters for a variety of accessories. When a user selects a specific accessory to use in a procedure, the user may then enter a serial number associated with that specific accessory into the control module. Using the serial number, the control module may access the relevant operating parameters for that specific accessory from its internal database. Since new accessories often come into the market, this database on the control module needs to be updated frequently to include the relevant operating parameters for each new accessory that a user may need. The need to frequently update a control module of the laser source may complicate and/or prolong procedures. Moreover, without operating parameters for an accessory stored in the control module, the user risks damaging the accessory, improper accessory operation, reduced accessory efficiency, or even exposing a patient to greater risk.

The systems, devices, and methods of the current disclosure may rectify some of the deficiencies described above, and/or address other aspects of the prior art.

SUMMARY

Examples of the present disclosure relate to, among other things, medical systems, devices, and methods. Each of the examples disclosed herein may include one or more of the features described in connection with any of the other disclosed examples.

According to one aspect, a method of controlling a laser delivery control console is disclosed. The method may include receiving at the control console electronically stored information from a radio frequency identification tag associated with a medical device. The method may also include converting, using at least one processor of the control console, the electronically stored information to a plurality of operating parameter threshold values. The plurality of threshold values may include maximum frequency values and maximum energy values for laser energy supplied by the laser delivery control console to the medical device. The method may further include preventing, in response to a command to adjust the energy or frequency of laser energy applied to the medical device, the delivery of laser energy with a frequency or energy value that exceeds one or more of the threshold values. The command may be generated by an action or series of actions on a user interface operably coupled to the laser delivery control console.

In other aspects of the present disclosure, the method of controlling a laser delivery control console may include one or more of the steps and/or features below. The plurality of threshold values may form an operating parameter matrix of the medical device. The control console may be configured to adjust the laser energy outputted to the medical device between a finite number of laser energy characteristics, and the finite number of laser energy characteristics may include a finite number of discreet frequency values and a finite number of discreet energy values. The maximum frequency and energy values may include maximum frequency and energy values for each of the finite number of discreet frequency values and a finite number of discreet energy values. The electronically stored information may be stored in 270 bytes or less electronic storage space. The medical device may be a laser fiber. Converting the electronically stored information to a plurality of threshold values may include using the electronically stored information to create a plurality of corner stone set point pairs defining an operating parameter matrix. The at least one processor may include a first data set corresponding to a matrix, the matrix may include a finite number of discreet frequency values along the matrix's horizontal axis and a finite number of discreet energy values along the matrix's vertical axis, and the matrix may be used to convert the electronically stored information to operating parameters for the medical device. Converting the electronically stored information to a plurality of operating parameter threshold values may include defining an operating parameter matrix including a maximum energy value for each of the finite number of discreet frequency values and a maximum frequency value for each of the finite number of discreet energy values. The medical device may be a laser fiber and the radio frequency identification tag may be coupled to a proximal end of the laser fiber.

In other aspects of the present disclosure, a method of controlling a laser delivery control console to deliver laser energy to a medical device is disclosed. The method may include accessing electronic information from an electronic memory device coupled to the medical device. The method may also include receiving at the control console electronically stored information from the electronic memory. The method may further include converting, using at least one processor of the control console, the electronically stored information to a series of operating parameters associated with the medical device. The plurality of operating parameters may include maximum frequency and energy values for laser energy supplied by the laser source to the medical device. The method may also include automatically preventing the delivery of laser energy with a frequency or energy level that exceeds one or more of the maximum frequency and energy values.

In other aspects of the present disclosure, the method of controlling a laser delivery control console to deliver laser energy to a medical device may include one or more of the steps and/or features below. The at least one processor may include stored electronic information of a uniform operating parameter matrix size, and the uniform operating parameter matrix size may include a matrix with a first axis including a finite number of discreet frequency values and second axis including a finite number of discreet energy values. The series of operating parameters may include a series of threshold set point pairs consisting of a discreet frequency value and a discreet energy value; and each of the threshold set point pairs may define the maximum frequency and energy values. Converting the electronically stored information to a series of operating parameters may not include accessing a database. The electronically stored information may include a plurality of corner stone set point pairs defining components of an operating parameter matrix for the medical device. Automatically preventing the delivery of laser energy with a frequency or energy level that exceeds one or more of the maximum frequency energy values may include limiting a range of discreet frequency and/or energy level settings available in the control console to adjust the output of laser energy from the laser source. The electronically stored information may include information defining locations within the uniform operating parameter matrix size, and the locations may be defined by a pair of values, and the pair of values may consist of one discreet frequency value and one discreet energy value.

In other aspects of the present disclosure, a medical device may include a body including a proximal end and a distal end. The body may be configured to receive laser energy and transport laser energy to the distal end. The medical device may also include an electronic memory device including representative electronic data stored on the electronic memory device. The electronic memory device may be coupled to the body. The representative electronic data may include data related to operating parameters including the maximum frequency and maximum energy levels of laser energy to be received by the medical device.

In other aspects of the present disclosure, the medical device may include one or more of the features below. The electronic memory device may be a radio frequency identification device. The electronic data may include data configured to be converted by a control console into an operating parameter matrix for the medical device. The operating parameters may consist of maximum frequency and maximum energy levels of laser energy to be received by the medical device. The electronic data may consist of 5 bytes of data.

Both the foregoing general description and the following detailed description are exemplary and explanatory only and are not restrictive of the features, as claimed. As used herein, the terms "comprises," "comprising," "having," "including," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal." As used herein, the terms "about," "substantially," and "approximately," indicate a range of values within +/−5% of a stated value.

BRIEF DESCRIPTION OF THE FIGURES

The accompanying drawings, which are incorporated in and constitute a part of this specification, illustrate various exemplary embodiments and together with the description, serve to explain the principles of the disclosure.

DETAILED DESCRIPTION

Examples of the present disclosure include systems, devices, and methods to facilitate the efficacy, efficiency, and safety of laser energy delivery during medical procedures. For example, aspects of the present disclosure may provide a user (e.g., a physician, medical technician, or other medical service provider) with the ability to more easily adjust and set the operating parameters of laser energy to be delivered to a laser accessory, such as a laser fiber. Some aspects of the present disclosure may be used in performing an endoscopic, hysteroscopic, or ureteroscopic procedure, such as, for example, a lithotripsy treatment, treating benign prostatic hyperplasia ("BPH"), or treating a cancerous tissue.

Reference will now be made in detail to examples of the present disclosure described above and illustrated in the accompanying drawings. Wherever possible, the same reference numbers will be used throughout the drawings to refer to the same or like parts.

The terms "proximal" and "distal" are used herein to refer to the relative positions of the components of an exemplary medical device or insertion device. When used herein, "proximal" refers to a position relatively closer to the exterior of the body or closer to an operator using the medical device or insertion device. In contrast, "distal" refers to a position relatively farther away from the operator using the medical device or insertion device, or closer to the interior of the body.

Figure 1:
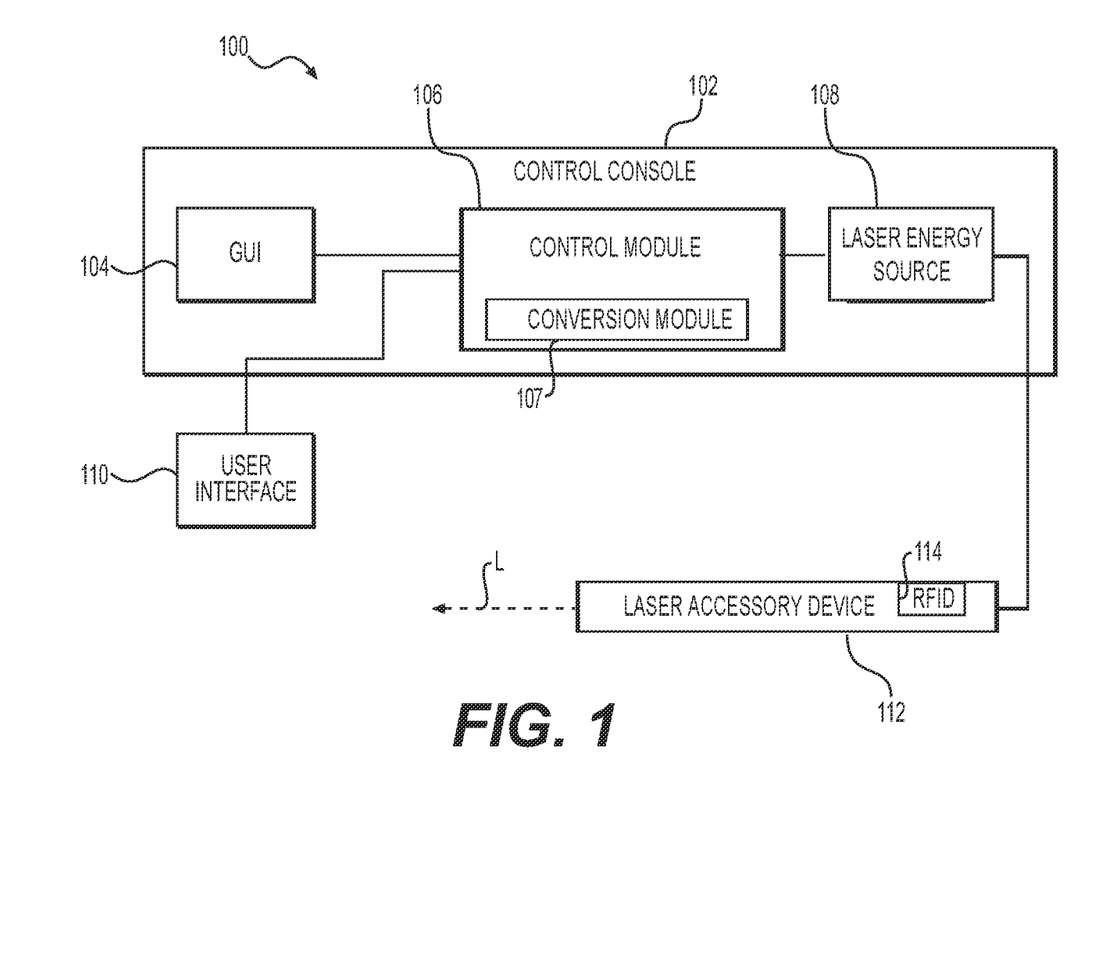
FIG. 1 illustrates a medical system, according to aspects of the present disclosure.

FIG. 1 illustrates a medical system 100 that includes a laser accessory device 112 and a laser control console 102. Control console 102 may include a graphical user interface or display 104, a control module 106, and a laser energy source 108. Control console 102 may be wire connected, wirelessly connected, or otherwise coupled to a user interface 110. In some examples, the user interface 110 may be incorporated into the control console 102. The medical system 100 may be configured to output laser energy from laser energy source 108 to a laser accessory device 112 for emission of a laser beam onto a target area.

Laser accessory device 112 may include one or more optical fibers to deliver laser energy (shown as arrow L) from laser energy source 108 to a distal end of the laser accessory device 112. As such, laser accessory device 112 may be used to deliver laser energy from laser energy source 108 to a lumen, tissue, or other material within a patient. In some examples, additional instruments or devices may be coupled to control console 102, such as an endoscope or other insertion device. In some examples, laser accessory device 112 may have a proximal end configured to connect to control console 102 and a distal end configured to deliver laser energy (L) to a patient's tissue.

User interface 110 may be a liquid crystal display (LCD), a touch screen display, or other electronic display. User interface 40 may display a menu with a variety of adjustable laser parameters, such as adjustable discreet frequency and energy levels for the output of laser energy from the laser energy source 108. User interface 110 may include one or more actuators, such as buttons, knobs, foot pedals, or other actuation mechanisms configured to communicate with control console 102.

Control console 102 may also include a laser accessing port (not shown) such that a laser accessory device 112, such as a laser fiber or other optical fiber, may be coupled to control console 102 to deliver laser energy to laser accessory 112. In some examples, control console 102 may be in communication with other accessory devices, such as an endoscope or a camera. Control console may be configured to transmit laser energy through a laser accessory device 112 to be delivered to the distal end of the laser accessory device 112. Control console 102 may be connected to and/or in communication with a power source, such as a battery or any other conventional power source known in the art, or the power source may be incorporated into the control console 102. An optical engine (not shown) may also be connected to and/or in communication with the control console 102 or incorporated into the control console 102, and the optical engine, power supply, and laser energy source 108 may supply energy to a laser fiber at a specific power level and frequency level.

Control module 106 within control console 102 may include an assembly of hardware, including a memory, a central processing unit ("CPU"), and/or a user interface (in addition to user interface 110). The memory may include any type of RAM or ROM embodied in a physical storage medium, such as magnetic storage including hard disk or magnetic tape; semiconductor storage such as solid state disk (SSD) or flash memory; optical disc storage; or magneto-optical disc storage; or other types of electronic memory. The CPU may include one or more processors for processing data according to instructions stored in the memory. The function of the processor may be provided by a single dedicated processor or by a plurality of processors. Moreover, the processor may include, without limitation, digital signal processor (DSP) hardware, or any other hardware capable of executing software. The user interface may include any type or combination of input/output devices, such as a display monitor, touchscreen, keyboard, and/or mouse. The processor may be configured to access wireless digital data, telephone, and/or Internet access through any other wireless communication medium, such as, for example, local or wide area Wi-Fi or Bluetooth connectivity. In some examples, the process may access a digital storage device or system via wireless communication, such as a cloud based storage system, to access information.

Laser source 108 may output a solid-state laser, continuous-wave (CW) laser, a pulsed laser, or other types of laser energy to be delivered to laser accessory device 112. In some examples, laser source 108 may include laser energy sources which operate at different wavelengths, infrared or visible light energy sources, a Holmium laser source, Carbon Dioxide laser source, Neodymium laser source, or other type of laser energy source. Control console 106 may be configured to adjust one or more characteristics of laser source 108. For example, control console 106 may be configured to adjust the frequency and/or the energy level of the laser energy output from laser source 108. In some examples, control console 106 may have a plurality of discreet frequency (for example, in Hertz) and energy (for example, in Joules) levels stored in control module 106 that may be selected by a user, using the user interface 110 and/or the graphical user interface 104, to adjust the laser energy output from laser source 108. The control module 106 may send instructions to user interface 110 and/or graphical user interface 104 to display a specific range of discreet frequency and energy levels to display and to allow a user to select. When a user selects a discreet frequency and energy level, the laser energy source 108 may output laser energy with the selected frequency and energy levels. In some examples, which may be for a pulsed laser energy output, control console 106 may provide a plurality of discrete set-point settings for the laser energy output of laser source 108, with each set-point setting consisting of a paired discreet frequency value and discreet energy value for the laser energy output of laser source 108.

Control console 102 may control the laser parameters supplied to laser accessory device 112. For example, control console 102 may include at least one processor, which may be within control module 106, which receives input from the graphical user interface 104 and/or the user interface 110 and processes the input. Control console 102 may include laser source 108, user interface 110, graphical user interface 104, and control module 106, each of which may be operable coupled together and/or may receive electronic information from and send electronic information to each of the other components. For example, a user may input a command using the user interface 104 to output laser energy at a specific frequency and energy level selected by the user, and the electronic command may be received by condole module 106, processed within control module 106, and then a corresponding electronic command may be sent to laser source 108 to output laser energy at the specified frequency and energy level. In some examples, a user may selectively adjust at least one of a laser energy, frequency, pulse width, wavelength, etc. via the user interface, such as a foot pedal assembly, keypad, mouse click, or touchscreen display, and control console 102 may output laser energy having the selected parameters to laser accessory device 112.

In some examples, an electronic database of information related to laser accessory devices and corresponding operating parameters may be electronically stored within control module 106. For example, an electronic database in control module 106 may include product identification numbers, serial numbers, product codes, or other forms of identification numbers used to identify specific laser accessory devices 112 and, stored in association with each identification number, may be a chart of operating parameters for each device. In some examples, the operating parameter chart for each laser accessory device may include discreet paired frequency and energy values that correspond to discreet energy and frequency set-point settings provided in control module 106 for adjusting the output of laser energy source 108.

Depending on the type of control console 102, control module 106, and laser energy source 108, the number of discreet frequency and energy output settings may be available for the control console 102 to change the characteristics of the laser energy output from laser energy source 108. In some examples, control console 102 may provide fifteen discreet frequency values (in Hertz) that may be selected by the user. Control console 102 may also, in some examples, provide eighteen discreet energy values (in Joules) that may be selected by the user. Each of these discreet frequency and energy setting values, or discreet set-point pairs of one frequency setting value and one energy setting value, may be described by a parameter matrix, such as matrix 200 shown in FIG. 2.

Figure 2:
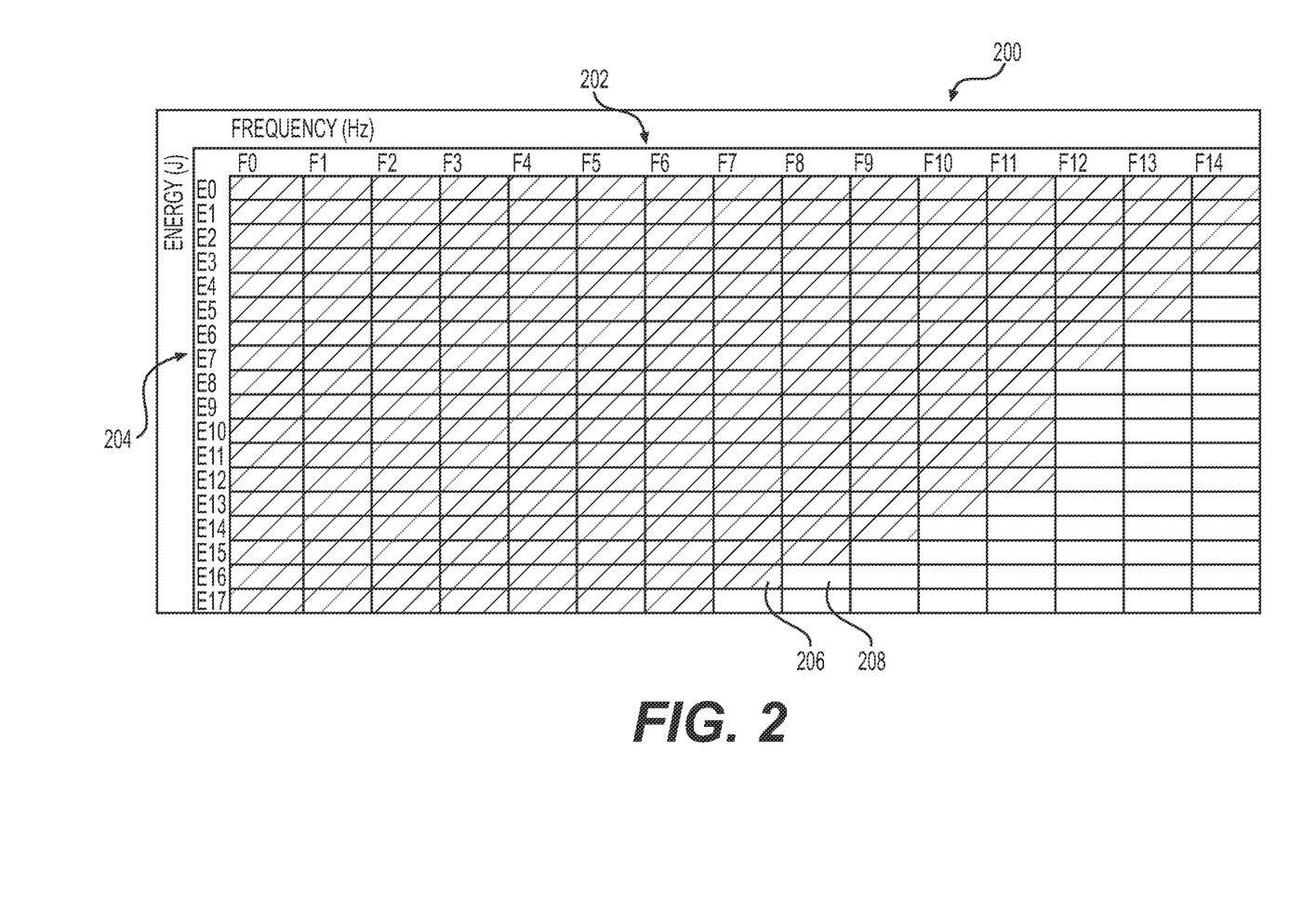
FIG. 2 illustrates an exemplary chart of operating parameters for a laser device, according to aspects of the present disclosure.

In the exemplary matrix 200, the fifteen discreet frequency setting values (frequency set-points) are defined as $F_i$ (i=0 to 14), and the eighteen discreet energy setting values (energy set-points) are defined as $E_j$ (j=0 to 17). Each discreet set-point pair may be described as an $F_i$, $E_j$ location on matrix 200, and may be represented as a box within matrix 200. The frequency setting values are shown along the horizontal axis 202, and the energy setting values are shown along the vertical axis 204. The cross-hatched boxes, such as box 206, designate operable energy and frequency value set point pairs for the laser accessory device 112 associated with matrix 200, and the white boxes or boxes without cross-hatching, such as white box 208, designate energy and frequency value set point pairs outside the laser accessory device's operating parameters and thus may damage the laser accessory device 112, render it inoperable, or fail to operate in accordance with the device's specifications. Thus, matrix 200 may define the operating parameters of a laser accessory device 112.

Each of the cross-hatched boxes shown in matrix 200 that borders at least one white box, such as, for example, cross-hatch box 206, may be defined as a "corner stone" set point pair. Each "corner stone" set point pair defines a threshold frequency value (one of F0-F14) for a discreet energy value (one of E0-E17) that defines a limit on the frequency operating range for that particular energy value, and a threshold energy value for a discreet frequency value that defines a limit on the energy operating range for that particular frequency. For example, corner stone set point pair 206 (F7, E16) in matrix 200 defines a maximum discreet energy value of E16 when the laser accessory device is operating at a frequency of F7, and a maximum discreet frequency value of F7 when laser accessory device 112 is operating at a discreet energy value of E16. Using matrix 200, control console 102 may define the operating parameters for the laser accessory device 112. In some examples, when operating a laser accessory device 112 associated with matrix 200, control console 102 may prevent the selection and/or the output of laser energy with a particular energy or frequency value that exceeds a threshold value defined by matrix 200, and thus prevent the user from selecting a discreet set point pair outside the operating range defined by each "corner stone" set point pair. In this manner, matrix 200 may be used by control console 102 to define the operating parameters for a particular laser accessory device 112. For example, an operating parameter matrix 200 may be received by control module 106 or retrieved from a database stored within control module 106, and the control module 106 may apply limitations to the user interface 110 and/or the graphical user interface 104 to prevent the user from selecting a discreet set point pair for the frequency (Fi) and energy (Ei) levels outside the operating parameters defined by matrix 200. In some examples, the user interface 110 and/or the graphical user interface 104 may display and allow a user to select only discreet set point pairs for the frequency (Fi) and energy (Ei) levels that are within the defined operating parameters of operating parameter matrix 200.

Figure 3:
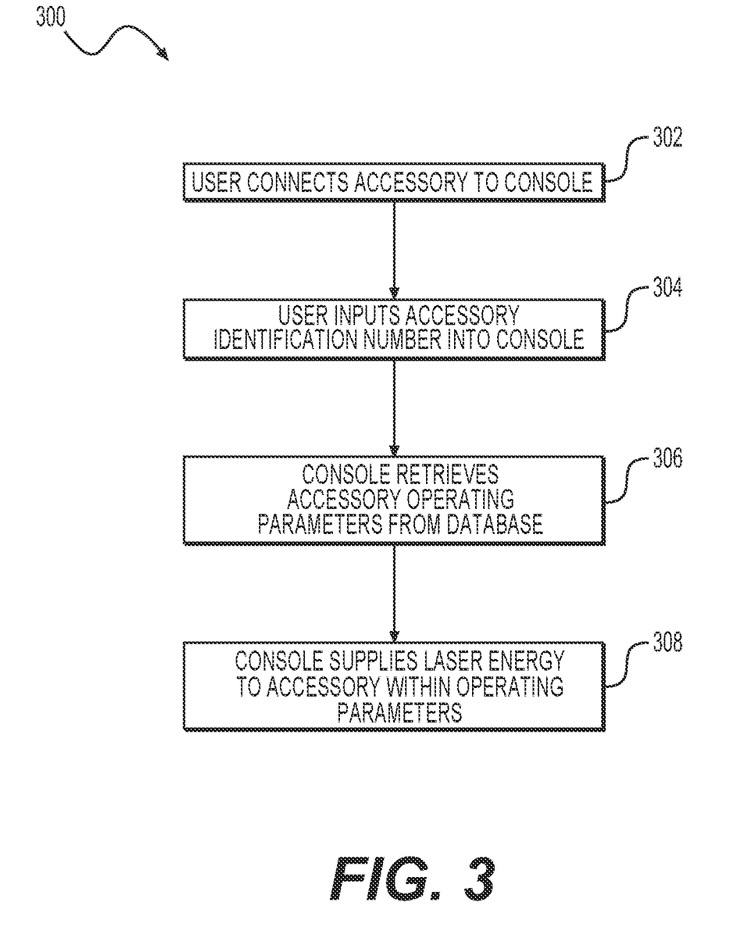
FIG. 3 is a flow diagram of a method of adjusting and setting a medical system, according to aspects of the present disclosure.

FIG. 3 illustrates a flow diagram 300 of a conventional method for applying operating parameters to a laser accessory device 112 using a control console 102. In step 302, the user connects laser accessory device 112 to control console 102. In some examples, a proximal end of laser accessory device 112 may be coupled to control console 102, for example a proximal end of a laser fiber may be inserted into an accessing port on control console 102. In step 304, the user may input an identification number, such as a serial or product number associated with the connected laser accessory device 112, into control console 102 using user interface 110. In step 306, control module 106 of control console 102 may receive and process the identification number and retrieve an operating parameter matrix, such as matrix 200, associated with laser accessory device 112 stored in a database within a control module 106.

Once the appropriate operating parameter matrix is retrieved, the control module 106 may set the operating parameter matrix 200 as the operating parameters for laser accessory device 112. When the operating parameter matrix 200 is set, control module 106 may prevent laser energy source 108 from outputting laser energy with a frequency and energy set point pair that is outside the corner stone set point pairs in matrix 200. For example, as shown in matrix 200, control module 106 would not allow the user to select a frequency of F9 with an energy level of E15 because this laser parameter set pair exceeds the threshold set by each corner stone pair of matrix 200. Depending on the type of laser accessory device 112, different threshold limits may be put on the laser energy source 108 by control module 106 to limit the maximum frequency and energy levels supplied to the laser accessory device 112. Similarly, different ranges of frequency (Fi) and energy (Ei) levels may be included in matrix 200 depending on the type of control console 102, laser energy source 108, and/or laser accessory device 108. Since control module 106 of control console 102 may have a limited amount of electronic storage to store an electronic database of laser accessory devices and associated operating parameter matrixes, alternative methods of storing operating parameters may allow a control module 106 to operate with a larger amount of laser accessory devices and may avoid the need to update databases stored within control module 106.

According to one aspect of this disclosure, operating parameters, or data associated with operating parameters, may be stored on laser accessory device 112. For example, laser accessory device 112 may include a radio frequency identification tag (RFID) 114 coupled to and/or embedded within laser accessory device 112. The RFID 114 may contain electronically-stored information associated with the laser accessory device 112, such as data associated with an operating parameter matrix for the laser accessory device 112. RFID devices 114 may be low power silicon devices that can be powered and communicate via a radiofrequency field. RFID 114 may enable wireless communication from an embedded RFID 114 chip coupled to or embedded within laser accessory device 112. RFID device 114 may be a non-volatile memory element for storing electronic information. For example, RFID device 114 may include read-only memory whose contents can be erased and reprogrammed using a pulsed voltage, such as EEPROM (typically 320 to 4096 bytes), and interface logic that handles communications. RFID 114 may be fabricated in a small disk that can be embedded into a laser accessory device. In some examples, a laser accessory device 112 may generate a low power localized radiofrequency field that may power RFID 114 when laser energy is supplied to the laser accessory device 112. Other formats/manners of manufacturing RFID devices can be used without departing from the scope of this disclosure. In some examples, electronic data may be stored on an RFID 114 coupled to laser accessory device 112, and the electronic data may include an operating parameter matrix 200 associated with laser accessory device 112. In other examples, laser accessory device 112 may include a memory device, such as a read-only memory, that connects to control console 102 via a wire connection between the memory device and the control console, such as a wire connection that connects the memory device of the laser accessory device 112 with the control console 102 via laser accessing port (not shown).

Figure 4:
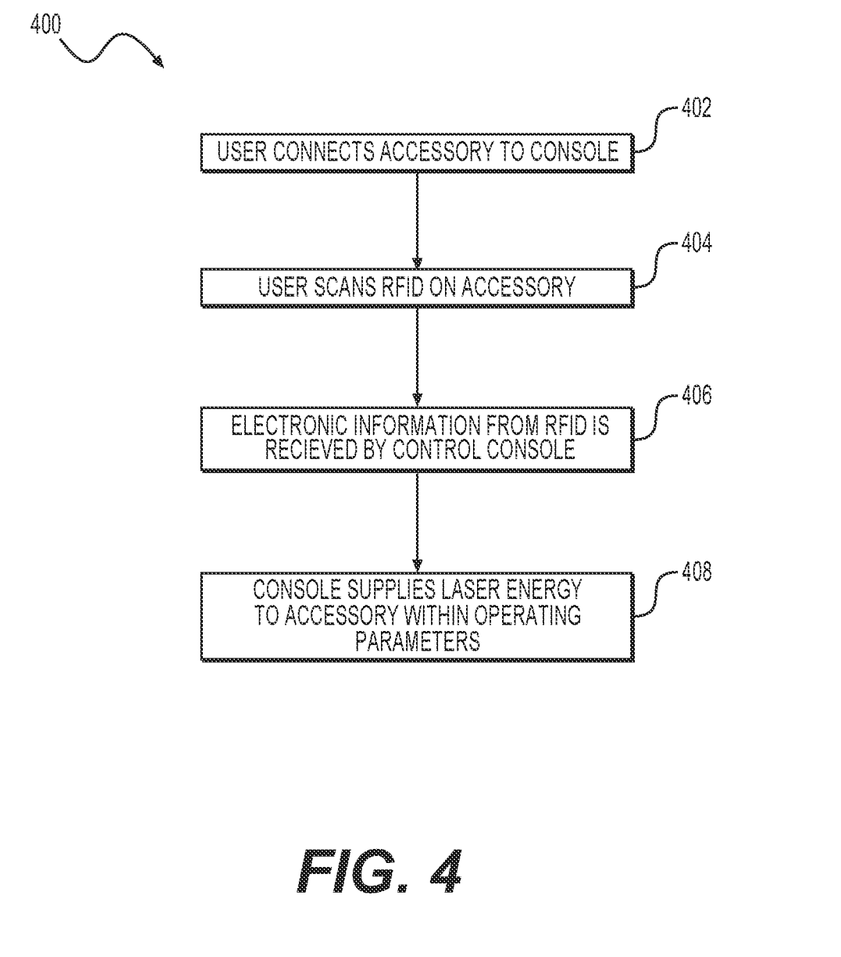
FIG. 4 is a flow diagram of a method of adjusting and setting a medical system, according to further aspects of the present disclosure.

FIG. 4 illustrates a flow diagram 400 of a method for applying operating parameters to a laser accessory device 112 using a control console 102 without a database of laser accessory devices and associated operating parameters stored within control console 102. In step 402, the user may connect an accessory device 112 to the control console 102. In the method of flow diagram 400, an entire operating parameter matrix 200 is stored in electronic data on an RFID 114 coupled to the laser accessory device 112.

In step 404, the user may scan the RFID 114 of the accessory device 112 using an RFID reader to upload the electronic information stored on RFID 114 to the RFID reader, and then the RFID reader may send the electronic information to control module 106. In some examples, an RFID reader may be incorporated into control console 102. In other examples, RFID reader may be electronically connected to control console 102. In step 406, the electronic information from RFID 114 is received by the control module 106. Since the electronic information from RFID 114 includes the entire operating parameter matrix 200, control module 106 may then implement operating parameter matrix 200 and proceed to step 408. When implementing operating parameter matrix 200, control module 106 may limit the frequency and energy level settings (Fi, Ei) available for the user to select based on operating parameter matrix 200. In step 408, the control console 102 supplies laser energy to laser accessory 112 within the accessory's operating parameters. In some cases, the amount of data required to store an entire operating parameter matrix 200 may exceed the storage space provided on an RFID 114, which would make the method of flow diagram 400 difficult to accomplish. In order to implement the method of flow diagram 400, RFID may need to have adequate electronic storage space to store data associated with the entire operating parameter matrix 200. In some cases, it may be beneficial to minimize the amount of data stored on the RFID in order to use RFID tags with less electronic storage space.

In some examples, RFID 114 of laser accessory device 112 may store operating parameter matrix representation data that, once received by a control module 106, may be converted to an operating parameter matrix 200 for the associated laser accessory device 112. For example, control module 106 may include a conversion module 107 configured to convert the matrix representation data to an operating parameter matrix 200. When representation data is stored in an RFID 114 of a laser accessory device 112, control module 106 may require a conversion module 107 to convert the representation data to an operating parameter matrix 200 for the respective laser accessory 112, and thus may avoid the need to store a database of laser accessories 112 and their respective operating parameter matrixes 200. In addition, by eliminating the need for an internal database of a plurality of laser accessory devices within control console 102, a user may avoid the task of updating the laser accessory devices database in the control console and may still use the control console effectively with a new laser accessory device 112, which may save time and increase efficiency of procedures.

Figure 5:
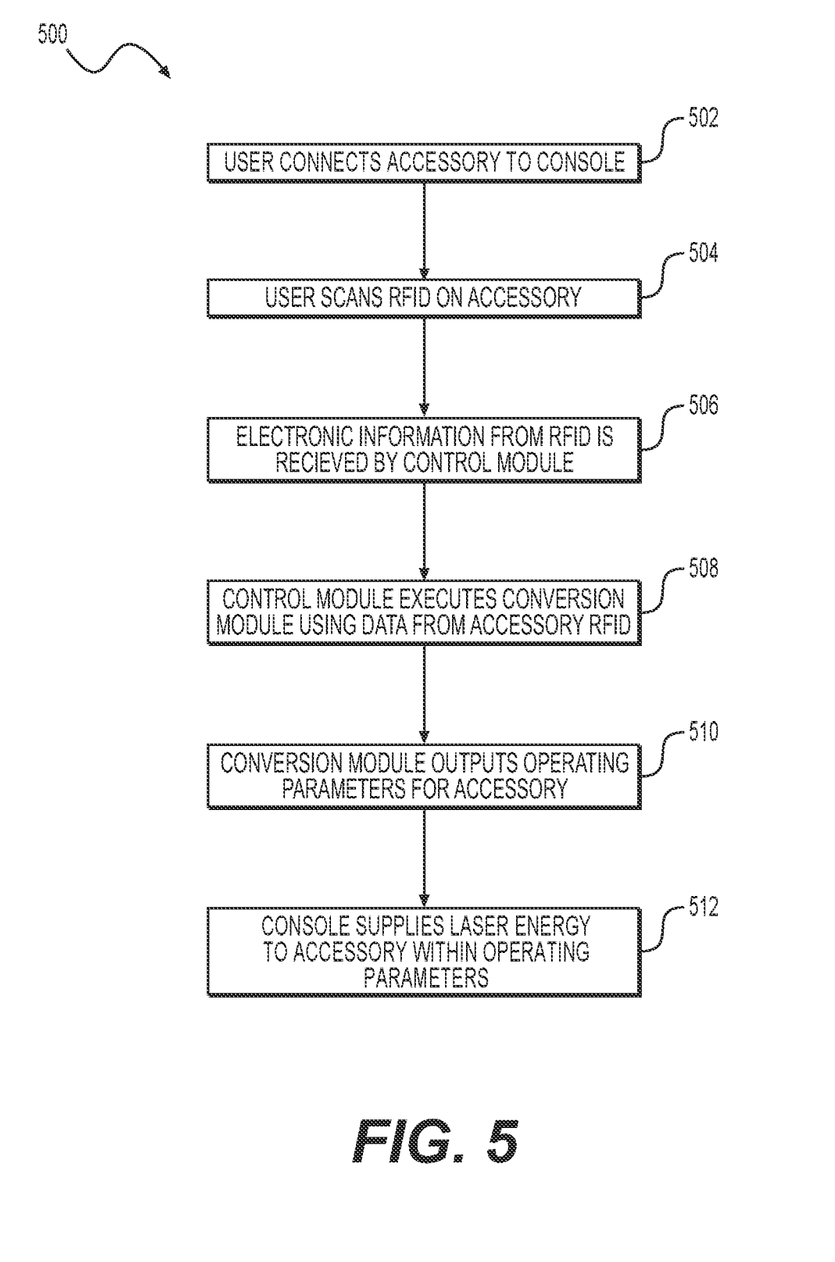
FIG. 5 is a flow diagram of a method for applying operating parameters to a laser accessory device, according to aspects of the present disclosure.

FIG. 5 illustrates a flow diagram 500 of a method for applying operating parameters to a laser accessory device 112 using a control console 102 without a database of laser accessory device identification numbers and associated operating parameters stored within control console 102. In step 502, the user may connect an accessory device 112 to the control console 102. In step 504, the user may scan the RFID 114 of the accessory device 112 using an RFID reader to upload the electronic information stored on RFID 114 to the RFID reader, and then the RFID reader may send the electronic information to control module 106. In step 506, the electronic information from RFID 114 is received by the control module 106 in control console 102. In step 508, the control module 106 may execute a conversion module 107 using the electronic data received from RFID 114.

Conversion module 107 may include software to convert the electronic data from RFID 114 to an operating parameter matrix 200 associated with laser accessory device 112. Once the conversion module 107 outputs an operating parameter matrix 200 in step 510, control module 106 applies the necessary operating parameters to safely operate the laser accessory 112. Accordingly, once the control module 102 receives and applies the operating parameter matrix 200 for laser accessory device 112 from conversion module 107, the control console 102 may supply laser energy to laser accessory 112 within the accessory's operating parameters. Storing representative electronic data that can be converted using conversion module 107 of control module 106 may allow RFID 114 to store less electronic data compared to storing an entire operating parameter matrix 200. The method for applying operating parameters to a laser accessory device 112 using a control console 102 shown in flow diagram 500 does not require accessing a database, such as a database of laser accessory device identification numbers and associated operating parameters stored within control console 102.

Figure 6:
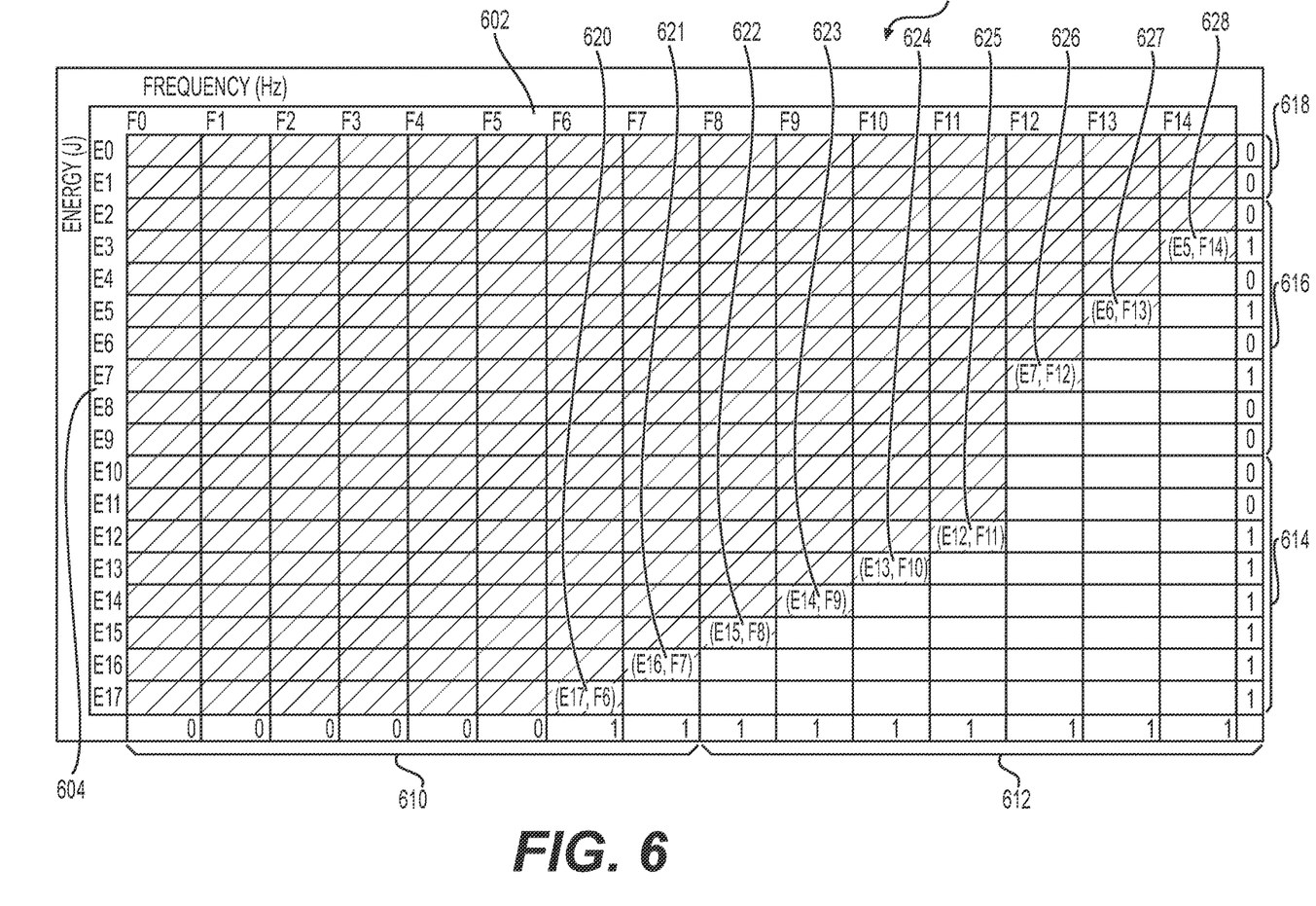
FIG. 6 is an exemplary operating parameter matrix, according to aspects of the present disclosure.

FIG. 6 illustrates an exemplary operating parameter matrix 600 similar to matrix 200 of FIG. 2. In the same manner as matrix 200, fifteen discreet frequency setting values (frequency set-points) are defined as F0-F14 along the horizontal axis 602, and the eighteen discreet energy setting values (energy set-points) are defined as E0-E17 along the vertical axis 604. Each discreet set-point pair of matrix 600 may be described as an Fi, Ej location on matrix 600. The cross-hatched boxes in matrix 600 designate operable energy and frequency value set point pairs for the laser accessory device associated with matrix 600, and the white boxes designate energy and frequency value set point pairs outside the laser accessory device's operating parameters.

In operating parameter matrix 600, cross-hatch boxes 620, 621, 622, 623, 624, 625, 626, 627, 628 each border at least one white box and may be defined as corner stone set point pairs. Each corner stone set point pair defines a threshold frequency value that defines a limit on the frequency (Fi) operating range for a particular energy value (Ei), and a threshold energy value (Ei) that defines a limit on the energy operating range for a particular frequency (Fi). For example, corner stone set point pair 621 is shown at matrix box (E16, F7), and indicates that at a frequency of F7 the maximum energy level is E16, and at energy level E16 the maximum frequency level is F7.

When a RFID 114 or other electronic storage medium is used to store all of the data associated with matrix 600, the data may include 270 data elements for each of the boxes within matrix 600, along with 33 data elements for each of the discreet frequency set points F0-F14 along the horizontal axis 602 and each of the discreet energy set points E0-E17 along the vertical axis 604. As an alternative to storing data associated with each box of matrix 600, RFID 114 or other electronic storage medium may store representative data that is configured to be converted into an operating parameter matrix using a conversion module 107 within control console 102.

For example, representative data stored on an RFID 114 may include only the parameters of the horizontal axis 602 and vertical axis 604 of matrix 600, i.e. discreet values E0-E17 and F0-F14, and each of the corner stone set point pairs, i.e. discreet set point pairs 620, 621, 622, 623, 624, 625, 626, 627, 628, totaling 51 total data elements consisting of the 18 data elements for E0-E17, 15 data elements for F0-F14, and eighteen data elements for each of the nine corner stone set point pairs 620, 621, 622, 623, 624, 625, 626, 627, 628. Accordingly, by storing only data elements associated with horizontal axis 602, vertical axis 604, and each corner stone set point pair 620, 621, 622, 623, 624, 625, 626, 627, 628, a total of 51 data elements may be used to store operating parameter matrix 600. By using a software algorithm within conversion module 107 of control module 106, the 18 data elements for E0-E17, fifteen data elements for F0-F14, and 18 data elements for each of the nine corner stone set point pairs 620, 621, 622, 623, 624, 625, 626, 627, 628 may be used to construct a complete operating parameter matrix 600 using a conversion module 107.

In some examples, a uniform operating parameter matrix size may be stored within a conversion module 107 of control console 102. For example, a uniform operating parameter matrix size may be a matrix with a horizontal axis 602 of 15 discreet data elements (F0-F14) and with a vertical axis 604 of 18 discreet data elements (E0-E17) that may be stored within conversion module 107 of control console 102. In some examples, control console 102 may be limited to a single set of discreet frequency settings (Fi) and a single set of discreet energy settings (Ei) available to the user for adjusting the output of laser energy source 108, and the single operating parameter matrix size available for that particular control console 102 may be stored within control module 106. By storing a uniform operating parameter matrix size in the control module 106, RFID 114 may not need to store the discreet values F0-F14 associated with the horizontal axis 602 and the discreet values E0-E17 associated with the vertical axis 604 of matrix 600, and thus may store only the information associated with each corner stone set point pair 620, 621, 622, 623, 624, 625, 626, 627, 628. Accordingly, when a uniform operating parameter matrix size is stored within control console 102, data elements E0-E17 and F0-F14 are predefined in the control console 102 and the RFID may only store the eighteen data elements associated with each corner stone set point pair 620, 621, 622, 623, 624, 625, 626, 627, 628. In this example, the conversion module 107 may use the eighteen data elements received from RFID 114 in conjunction with the uniform operating parameter matrix size stored within the conversion module 107 to construct operating parameter matrix 600.

In another example where a uniform operating parameter matrix size is stored within control console 102, representative data stored on RFID 114 may consist of five bytes of electronic data (or 34 total bits). As is known in the art, a byte of data consists of an eight digit binary number. As shown in FIG. 6 as bytes 610, 612, 614, 616, 618, five bytes of data may be used to designate where in a uniform operating parameter matrix size of fifteen by eighteen (shown in FIG. 6) each of the corner stone set point pairs are located within matrix 600. Note bytes 610, 612, 614, 616, 618 are provided in an additional column and an additional row of matrix 600, however this row and column containing bytes 610, 612, 614, 616, 168 is purely for illustrative purposes and is not a part of operating parameter matrix 600. In FIG. 6, bytes 610, 612 designate each discreet frequency value (Fi) along horizontal axis 602 that includes a corner stone set point pair with a one (values F6-F14), and each frequency value along horizontal axis 602 that does not include a corner stone set point pair with a zero (values F0-F5). Similarly, bytes 614, 616, 618, designate each discreet energy value (Ei) along vertical axis 604 that includes a corner stone set point pair with a one (values E3, E5, E7, and E12-E17), and each energy value along vertical axis 604 that does not include a corner stone set point pair with a zero (values E0-E3, E4, E6, and E8-E11). Accordingly, operating parameter matrix 600 may be represented by a bitmap on 16 bits and 20 bits, or with 5 bytes of data, when console 102 stores a uniform operating parameter matrix size that corresponds to operating parameter matrix 600. In this example, conversion module 107 may include software to convert bytes 610, 612, 614, 616, 618 associated with the location of each corner stone set point pair 620, 621, 622, 623, 624, 625, 626, 627, 628 into operating parameter matrix 600. Thus, for example, laser accessory device 112 may store only bytes 610, 612, 614, 616, 618 on RFID 114.

For example, for illustrative purposes, a hypothetical control console 102 includes a uniform operating parameter matrix size of fifteen by eighteen (e.g. the size of matrix 600 in FIG. 6), with the horizontal axis representing frequency values F0-F14 and the vertical axis representing energy values E0-E17. Implementing the systems and methods disclosed herein, an exemplary laser accessory device 112 includes an RFID 114 with five bytes of data stored on the RFID 114. Each byte of data corresponds to bytes 610, 612, 614, 616, 618. The first byte 610 reads "00000011" and corresponds to columns F0-F6, and thus each of columns F5 and F6 includes a corner stone set point pair. The second byte 612 reads "11111111" and corresponds to columns F7-F14, and thus each of columns F7-F14 includes a corner stone set point pair. The third byte 614 reads "11111100" and corresponds to rows E17 to E10, and thus each of columns E17-E12 includes a corner stone set point pair. The fourth byte 616 reads "00101010" and corresponds to rows E9-E2, respectively, and thus each of columns E7, E5, and E3 includes a corner stone set point pair. Lastly, the fifth byte 618 reads "00000000", of which only the first two digits are used to construct matrix 600. Thus, since the first two digits of the fifth byte 618 corresponds to rows E1 and E0, "00" indicates that neither row E1 nor row E0 includes a corner stone set point pair. Then, by matching each of the marked columns from the first and second bytes with each of the marked rows from the third, fourth, and fifth bytes, in the order in which they occur, i.e. moving from F0-F14 for the first and second bytes and moving from E17 to E0 for the third, fourth and fifth bytes, a system, such as control module 106 of control console 102, can construct matrix 600 by marking each corner stone set point pair 620, 621, 622, 623, 624, 625, 626, 627, 628 within the uniform operating parameter matrix size of fifteen by eighteen. The control module 106 may then set the appropriate frequency and energy thresholds for that particular laser accessory device 112 using the constructed matrix 600.

While the above discussion is directed to specific methods for storing operating parameter matrixes related to laser delivery devices, the present disclosure is not so limited. For example, matrixes 200 and 600 are only exemplary, and the above-described methods may be applied to operating parameter matrixes of any size. In some examples, the operating parameters stored on laser accessory device 112 may include power source output values indicating an operable range or value of power to be supplied to laser accessory device 112.

While principles of the present disclosure are described herein with reference to illustrative examples for particular applications, it should be understood that the disclosure is not limited thereto. Those having ordinary skill in the art and access to the teachings provided herein will recognize additional modifications, applications, embodiments, and substitution of equivalents all fall within the scope of the features described herein. Accordingly, the claimed features are not to be considered as limited by the foregoing description.

We claim:

1. A laser delivery console, comprising:
   a memory comprising a uniform operating parameter matrix comprising a plurality of frequency values and a plurality of energy setting values for a plurality laser accessory devices; and
   a control module comprising processing circuitry configured to:
      receive, from a radio frequency identification (RFID) tag associated with a one of the plurality of laser accessory devices, a plurality of corner stone set point pairs, wherein the plurality of corner stone set point pairs defines a maximum one of the plurality of frequency values for each one of the plurality of energy setting values for the one of the plurality of laser accessory devices;
      generate an operating parameter matrix for the one of the plurality of laser accessory devices from the uniform operating parameter matrix and the plurality of cornerstone set point pairs, wherein the operating parameter matrix comprises a subset of the plurality of frequency values and a subset of the plurality of energy setting values; and
      prevent, in response to a command to adjust an amount of energy or a frequency of laser energy applied to the one of the plurality of laser accessory devices, the delivery of laser energy with a combination of frequency and energy value that exceeds one of the subset of the plurality of frequency values and/or one of the subset of the plurality of energy setting values, wherein the command is generated by an action or series of actions on a user interface operably coupled to the laser delivery control console.

2. The laser delivery console of claim 1, the control module further configured to adjust the laser energy outputted to the medical device between a finite number of combinations frequency and energy values, wherein the finite number of frequency and energy values are identified based on the operating parameter matrix.

3. The laser delivery console of claim 1, wherein the laser delivery control console is configured to output laser energy having each of the finite number of combinations frequency and energy values, wherein the finite number of frequency and energy values are identified based on the operating parameter matrix.

4. The laser delivery console of claim 1, wherein the plurality of corner stone set point pairs is stored in five (5) bytes or less electronic storage space.

5. The laser delivery console of claim 1, wherein the laser accessory device comprises an optical fiber.

6. The laser delivery console of claim 5, comprising the laser accessory device.

7. The laser delivery console of claim 6, wherein the RFID tag is embedded within the laser accessory device.

8. The laser delivery console of claim 1, wherein the uniform operating parameter matrix comprises a plurality of rows and columns and wherein the plurality of corner stone set point pairs comprises a set point pair for each column of the matrix.

9. At least one non-transitory machine readable medium comprising a uniform operating parameter matrix and a plurality of instructions that in response to being executed by circuitry of a laser delivery console, cause the laser delivery console to:
   receive, from a radio frequency identification (RFID) tag embedded within a laser accessory device coupled to the laser delivery console, a plurality of corner stone set point pairs, wherein the plurality of corner stone set point pairs defines a maximum one of the plurality of frequency values for each one of the plurality of energy setting values, wherein the laser accessory device is a one of a plurality of laser accessory devices;
   generate an operating parameter matrix from the uniform operating parameter matrix and the plurality of cornerstone set point pairs, wherein the operating parameter matrix comprises a subset of the plurality of frequency values and a subset of the plurality of energy setting values for the one of the plurality laser accessory devices, wherein the uniform operating parameter matrix comprises a plurality of frequency values and a plurality of energy setting values for the plurality laser accessory devices; and
   prevent, in response to a command to adjust an amount of energy or a frequency of laser energy applied to the laser accessory device, the delivery of laser energy with a combination of frequency and energy value that exceeds one of the subset of the plurality of frequency values and/or one of the subset of the plurality of energy setting values, wherein the command is generated by an action or series of actions on a user interface operably coupled to the laser delivery control console.

10. The at least one non-transitory machine readable medium of claim 9, comprising instructions that in response to being executed by the circuitry further cause the laser delivery console to adjust the laser energy outputted to the medical device between a finite number of combinations frequency and energy values, wherein the finite number of frequency and energy values are identified based on the operating parameter matrix.

11. The at least one non-transitory machine readable medium of claim 9, comprising instructions that in response to being executed by the circuitry further cause the laser delivery console to output laser energy having each of the finite number of combinations frequency and energy values, wherein the finite number of frequency and energy values are identified based on the operating parameter matrix.

12. The at least one non-transitory machine readable medium of claim 9, wherein the plurality of corner stone set point pairs is stored in five (5) bytes or less electronic storage space.

13. The at least one non-transitory machine readable medium of claim 9, wherein the laser accessory device comprises an optical fiber.

14. The at least one non-transitory machine readable medium of claim 9, wherein the uniform operating parameter matrix comprises a plurality of rows and columns and wherein the plurality of corner stone set point pairs comprises a set point pair for each column of the matrix.

15. A method for a controller of a laser delivery console, comprising:
   receiving, from a radio frequency identification (RFID) tag associated with a laser accessory device coupled to the laser delivery console, a plurality of corner stone set point pairs, wherein the plurality of corner stone set point pairs defines a maximum one of the plurality of frequency values for each one of the plurality of energy setting values wherein the laser accessory device is a one of a plurality of laser accessory devices;
   generating an operating parameter matrix from a uniform operating parameter matrix and the plurality of cornerstone set point pairs, wherein the operating parameter matrix comprises a subset of the plurality of frequency values and a subset of the plurality of energy setting values for the one of the plurality laser accessory devices, wherein the uniform operating parameter matrix comprises a plurality of frequency values and a plurality of energy setting values for the plurality laser accessory devices; and
   preventing, in response to a command to adjust an amount of energy or a frequency of laser energy applied to the laser accessory device, the delivery of laser energy with a combination of frequency and energy value that exceeds one of the subset of the plurality of frequency values and/or one of the subset of the plurality of energy setting values, wherein the command is generated by an action or series of actions on a user interface operably coupled to the laser delivery control console.

16. The method of claim 15, further comprising adjusting the laser energy outputted to the medical device between a finite number of combinations frequency and energy values, wherein the finite number of frequency and energy values are identified based on the operating parameter matrix.

17. The method of claim 15, further comprising outputting laser energy having each of the finite number of combinations frequency and energy values, wherein the finite number of frequency and energy values are identified based on the operating parameter matrix.

18. The method of claim 15, wherein the plurality of corner stone set point pairs is stored in five (5) bytes or less electronic storage space.

19. The method of claim 15, wherein the laser accessory device comprises an optical fiber.

20. The method of claim 15, wherein the uniform operating parameter matrix comprises a plurality of rows and columns and wherein the plurality of corner stone set point pairs comprises a set point pair for each column of the matrix.

* * * * *